United States Patent [19]

Leonard

[11] Patent Number: 4,846,177
[45] Date of Patent: Jul. 11, 1989

[54] COMBINATION FLUID PATH AND MOUNT FOR HEAT EXCHANGER

[75] Inventor: Ronald J. Leonard, Ann Arbor, Mich.

[73] Assignee: Minnesota Mining and Manufacturing Company, St. Paul, Minn.

[21] Appl. No.: 219,325

[22] Filed: Jul. 15, 1988

[51] Int. Cl.$^4$ .............................................. A61F 7/00
[52] U.S. Cl. ..................................... 128/400; 165/76; 604/113
[58] Field of Search ........... 128/399, 400, 403, 204.17, 128/203.26; 604/53; 165/76; 138/89

[56] References Cited

U.S. PATENT DOCUMENTS

| | | | |
|---|---|---|---|
| 1,046,298 | 12/1912 | Hurley | 165/76 |
| 2,000,653 | 5/1935 | Wilkinson | 165/76 |
| 2,836,918 | 6/1958 | Pula et al. | 138/89 |
| 3,315,734 | 4/1967 | Nadolny | 128/400 |
| 3,457,987 | 7/1969 | Lampe | 165/76 |
| 3,640,340 | 2/1972 | Leonard et al. | 128/400 |

FOREIGN PATENT DOCUMENTS 2607707 7/1988 France .................................. 604/53

*Primary Examiner*—Edward M. Coven
*Assistant Examiner*—Small D.
*Attorney, Agent, or Firm*—Donald M. Sell; Walter N. Kirn; Stephen W. Bauer

[57] ABSTRACT

A combination fluid path and mount for a heat exchanger of the type used to cool or heat blood or solution for cardioplegia by transferring heat between the blood or solution and a heat-exchanging fluid. The heat exchanger has an inner surface defining a passageway in which heat-exchanging fluid circulates. The combination comprises a body of generally flexible-resilient material having a periphery adapted to be received in the passageway of the heat exchanger. A bracket is provided for mounting the body on a support. The body has heat-exchanging fluid inlet and outlet passageways, each opening through the periphery for circulating the heat-exchanging fluid to the passageway of the heat exchanger. A fixing-sealing mechanism is provided for removably fixing the heat exchanger to the body and sealing between the body and the inner surface of the heat exchanger. The fixing-sealing mechanism expands a portion of the periphery of the body against the inner surface of the heat exchanger to form a seal therebetween and to hold the heat exchanger on the body. Heat exchangers specifically designed for use with the combination are also disclosed.

18 Claims, 4 Drawing Sheets

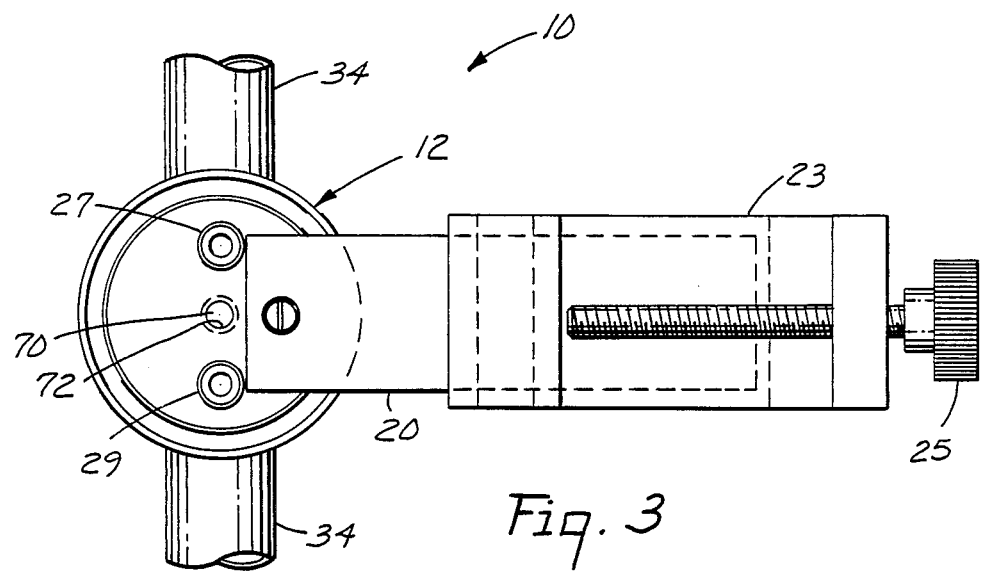
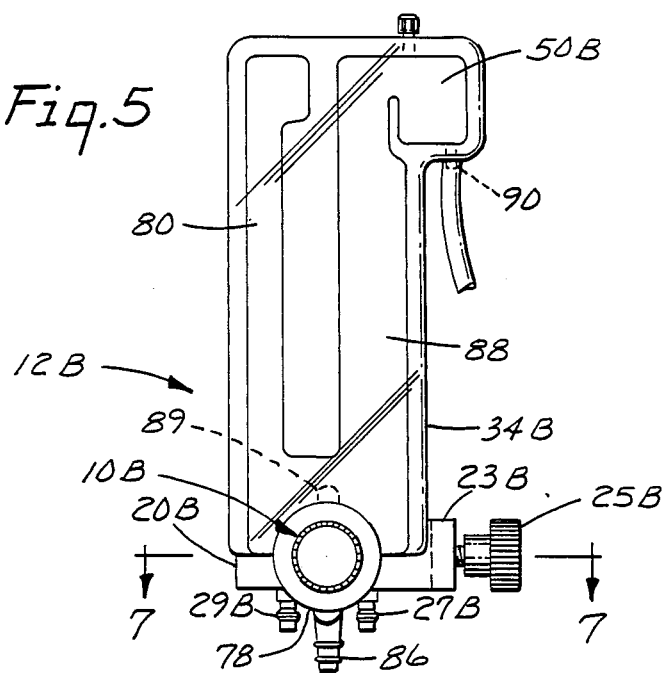

COMBINATION FLUID PATH AND MOUNT FOR HEAT EXCHANGER

The invention relates generally to mounting devices and connectors for fluid conduits, and more particularly to a combination heat-exchanging fluid path and mount for a heat exchanger of the type used to cool and heat blood or solution for cardioplegia by transferring heat between the blood or cardioplegia solution and the heat-exchanging fluid.

BACKGROUND OF THE INVENTION

Heat exchangers used to cool and heat blood or solution for cardioplegia (techniques for reducing the risk of damage to the heart by cooling and administering drugs to the heart) have included inlet and outlet fittings for both the heat-exchanging fluid or coolant (e.g., water) and the blood or cardioplegia solution, and suitable tubing for supplying or removing the fluids has been separately connected to each fitting. Typically, the fittings for tubing carrying the heat-exchanging fluid are of the quick-disconnect type, such as sold under the trade designation "Hansen Fittings" by The Hansen Manufacturing Co. of Cleveland, Ohio, wherein a sleeve adjacent one end of the tubing presses ball bearings held in the end of the tubing radially inwardly into an annular channel in the male portion of the fitting on the heat exchanger, thereby securing the tubing to the heat exchanger. The sleeve is movable axially with respect to the tubing to allow the ball bearings to move radially outwardly from the channel, thereby releasing the male portion of the fitting so that the tubing may be separated from the heat exchanger. The fittings are relatively large and heavy compared to the size of modern heat exchangers, and must be individually connected and disconnected to the heat exchanger. The fittings do not ordinarily hold the heat exchanger in a suitable position for use so that the heat exchanger must be separately clamped to a support stand, and the weight of the fittings increases the difficulty of supporting the heat exchanger.

SUMMARY OF THE INVENTION

The present invention provides a combination fluid path and mount which is useful for holding a heat exchanger of the type used to cool and heat blood or solution for cardioplegia and for supplying a heat-exchanging fluid, such as water, to the heat exchanger; that eliminates the need to connect and reconnect a number of individual heat-exchanging fluid conduits to the heat exchanger; and which facilitates simultaneous mounting of the heat exchanger and connecting of heat-exchanging fluid conduits to the heat exchanger.

Generally, a combination fluid path and mount of the present invention is designed for mounting and supplying heat-exchanging fluid to a heat exchanger of the type used to cool and heat blood or solution for cardioplegia by transferring heat between the blood or solution and heat-exchanging fluid. The heat exchanger has an inner surface defining a passageway in which heat-exchanging fluid flows. The combination comprises a body of generally flexible-resilient material having a periphery adapted to be received in the passageway of the heat exchanger, and means for mounting the body on a support. The body has heat-exchanging fluid inlet and outlet passageways, each opening through the periphery for circulating the heat-exchanging fluid to the heat exchanger. Fixing-sealing means are provided for removably fixing the heat exchanger to the body and sealing between the body and the inner surface of the heat exchanger. The fixing-sealing means includes means for expanding a portion of the periphery of the body against the inner surface of the heat exchanger to form a seal therebetween and to hold the heat exchanger on the body.

In a second aspect of this invention, a heat exchanger is designed to be mounted on the aforesaid combination fluid path and mount. The heat exchanger comprises an outer case having an inlet and outlet for blood or cardioplegia solution, and a barrier sealingly connected to the case for separating the blood or cardioplegia solution from the heat-exchanging fluid while permitting heat transfer through the barrier. The barrier has an inner surface defining a passageway in which heat-exchanging fluid may be circulated, and which is adapted to receive the body of the combination fluid path and mount for mounting the heat exchanger thereon and providing heat-exchanging fluid to the heat exchanger. The inner surface of the barrier is adapted for sealing engagement with an expandable portion of the body of the combination fluid path and mount.

Other features will be in part apparent and in part pointed out hereinafter.

BRIEF DESCRIPTION OF THE DRAWINGS

The present invention will be further described with reference to the drawings wherein corresponding reference characters indicate corresponding parts throughout the several views of the drawings, and wherein:

FIG. 3 is a rear elevation of the combination and heat exchanger of FIGS. 1 and 2;

FIG. 5 is a front elevation of additional embodiments of the combination and heat exchanger of the invention;

DETAILED DESCRIPTION

Figure 1:
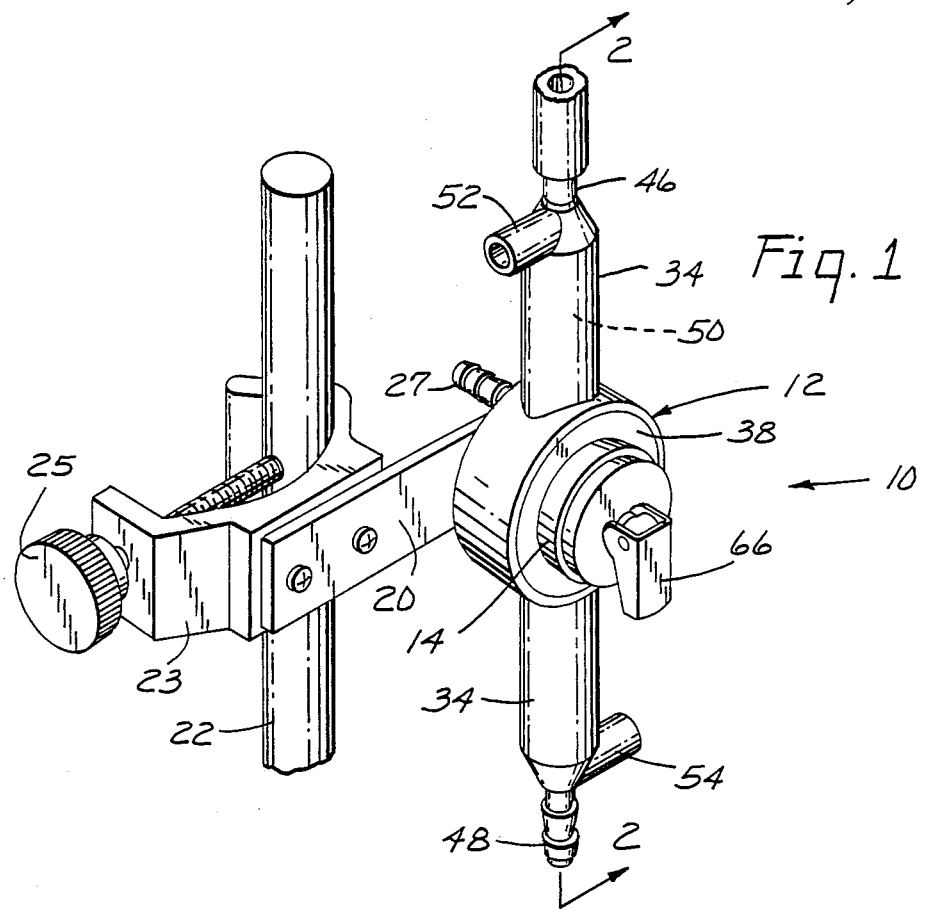
FIG. 1 is perspective view of a combination fluid path and mount of the present invention, on which a cardioplegia heat exchanger of the invention is mounted.

Now referring to the drawings, a combination fluid path and mount of the present invention is designated in its entirety by the reference numeral 10. The combination fluid path and mount 10 is particularly designed to hold a heat exchanger generally designated 12 of the type used to cool and heat blood or solution for cardioplegia and for supplying heat-exchanging fluid, such as water, to the heat exchanger so that heat may be transferred between the blood or solution and the heat-exchanging fluid. The combination fluid path and mount 10 provides a mechanism for quickly connecting and disconnecting heat exchangers, which must be sterile and may be disposable, to the combination, which may be reusable.

Figure 2:
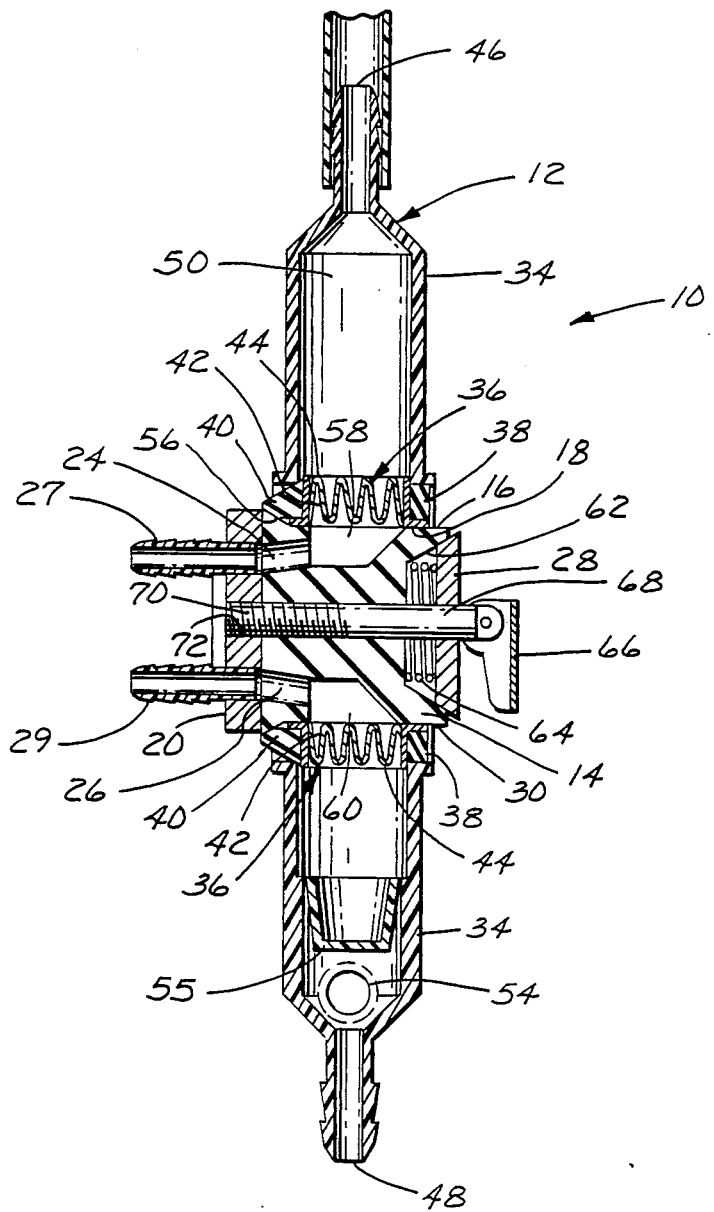
FIG. 2 is a cross-sectional view substantially along line 2—2 of FIG. 1.

As shown in FIGS. 1 and 2, the combination 10 generally comprises a generally cylindricl body 14 of generally flexible-resilient material having a periphery 16 adapted to be received in a fluid-path portion or passageway 18 of the heat exchanger 12, in which the heat-exchanging fluid circulates. Means (e.g., bracket 20) is provided on the inner or rear end (e.g., the left end in FIG. 2) of the body 14 for mounting or clamping the body on a support stand 22. More specifically, clamp means, such as a generally C-shaped clamp 23 and operating screw 25, is provided on the end of the bracket 20 remote from the body 14 for clamping the support stand 22. As shown in FIG. 2, the body 14 has heat-exchanging fluid inlet and outlet passageways 24 and 26, each opening at 58 and 60, respectively, through the periphery 16 of the body for circulating heat-exchanging fluid to the heat exchanger 12. Hose fittings 27 and 29, communicating with the inlet and outlet passageways 24 and 26, respectively, are provided on the bracket 20. Fixing-sealing means is provided for removably fixing the heat exchanger 12 to the body 14 and sealing between the body and heat exchanger. The fixing-sealing means includes tapered means (e.g., frustoconical member 28) for expanding a portion 30 of the periphery of the body 14 radially outwardly against an inner surface 42 of the heat exchanger 12 to form a seal therebetween and to hold the heat exchanger on the body. Alternatively, the fixing sealing means may include suitable non-tapered means, such as a cylindrical or other shaped member (not shown), for expanding the portion 30 of the body 14 laterally outwardly against the inner surface 42 of the heat exchanger.

The heat exchanger 12 has a generally cylindrical passageway 18 in which the heat-exchanging fluid may be circulated, and which is adapted for closely receiving the body 14 to mount the heat exchanger on the body such that the heat-exchanging fluid is supplied to the heat exchanger via the inlet passageway 24 and removed from the heat exchanger via the outlet passageway 26. The heat exchanger 12 includes a generally transparent outer case 34 of synthetic resin material (e.g., acrylic resin or polycarbonate), and an undulated, annular barrier 36 (FIG. 2) in the case for separating the blood or cardioplegia solution from the heat-exchanging fluid while permitting heat transfer through the barrier. The case 34 and barrier 36 are sealingly interconnected by annular seals 38 and 40 (e.g., of urethane or silicone sealant) adjacent opposite end portions of the barrier. The end portions of the barrier 36 have generally L-shaped cross sections in the direction longitudinally of the barrier forming flat and cylindrical surfaces adapted for sealing engagement with the seals 38 and 40. The barrier 36 is preferably formed of material having a high thermal conductivity, e.g., stainless steel, and has an inner undulated surface 42 defining the body-receiving and fluid-circulating passageway 18 as generally cylindrical and complementary to the body 14, and an outer undulated surface 44 in the case 34 along which the blood or cardioplegia solution flows through the case between an inlet 46 at an "upper" end of the case and an outlet 48 at the opposite or "lower" end of the case. The inner and outer undulated surfaces 42 and 44 of the barrier 36 form a plurality of generally annular channels running circumferentially around the barrier. It will be observed that if the body 14 is sufficiently closely received within the passageway 18 formed by the inner surface 42 of the barrier 36, the heat-exchanging fluid will be forced into the annular channels formed by the undulations of the inner surface to facilitate heat transfer between the fluid and the blood or cardioplegia solution across the barrier.

The case 34 includes a bubble trap 50 formed by the relatively large internal space adjacent the upper or inlet end of the blood or cardioplegia solution path for separating and trapping gas from the blood or solution so that the gas may be vented through a gas relief passageway 52 and manually actuatable valve (not shown) when sufficient gas has collected in the bubble trap. A thermowell 54 is provided adjacent the lower end of the case 34 for receiving a temperature sensor (not shown) so that the temperature of the blood or cardioplegia solution flowing from the heat exchanger may be measured. A suitable filter screen 55 may be positioned within the case 34 between the barrier 36 and the outlet 48 for filtering the blood or cardioplegia solution flowing through the heat exchanger 12. The heat exchanger 12 is adapted to be turned on the cylindrical body 14 between a priming position wherein the bubble trap 50 is positioned below the body 14 and blood or cardioplegia solution flows upwardly from the inlet 46 to fill the heat exchanger and a ready position (FIGS. 1 and 2) wherein the bubble trap is positioned above the body and blood or solution flows downwardly from the inlet through the heat exchanger and gas bubbles migrate upwardly against the flow into the bubble trap.

The cylindrical body 14 of the combination fluid path and mount 10 is formed of generally elastomeric material, e.g., silicone rubber or urethane having a Shore A durometer of between 60 and 90. The body 14 is preferably flared radially outwardly at 56 (FIG. 2) adjacent the bracket 20 to provide a seal between the flared portion 56 of the body and the corresponding end of the barrier 36. The heat-exchanging fluid inlet and outlet passageways 24, 26 have openings 58 and 60, respectively, formed in the circumferential surface of the body 14 along opposite sides of the body for supplying heat-exchanging fluid to the heat exchanger 12 and removing heat-exchanging fluid from the heat exchanger. The openings 58, 60 are preferably elongate in the direction longitudinally or axially of the body 14 so that the heat-exchanging fluid flows along substantially the entire inner surface 42 of the barrier 36 between the inlet and outlet openings.

The body 14 has a generally cylindrical or frustoconical recess 62 extending substantially coaxially into the body from the outer end of the body, that is, the end which is opposite the bracket 20, toward the bracket. The frustoconical member 28 and recess 62 are sized and configured such that when the member is inserted in the recess 62, the portion 30 of the body 14 adjacent the recess is expanded radially outwardly by the member to form a seal between portion 30 and the end of the heat exchanger barrier 36 adjacent the outer end of the body. Spring means, e.g., coil spring 64, is provided in the recess 62 between the member 28 and the base of the recess for biasing the member longitudinally or axially outwardly (i.e., rightwardly in FIG. 2) from the recess 62 of the body 14 to a non-sealing position (FIG. 2) wherein portion 30 is not expanded radially outwardly so that the heat exchanger 12 can be placed on the body with the body received in the heat-exchanging fluid passageway 18 of the heat exchanger and the heat exchanger can be removed from the body. The member 28 is movable against the spring bias longitudinally or axially inwardly (i.e., leftwardly in FIG. 2) into the recess 62 to a sealing position wherein the portion 30 of the body adjacent the recess is expanded radially outwardly by the member to hold and seal the heat exchanger.

Preferably, releasable locking means is provided for pulling the member 28 toward the bracket 20 into the recess 62 and holding it in the recess in its sealing position. For example, the releasable locking means may include an overcenter locking mechanism 66 for securely holding the member 28 in the recess 62, and an adjusting bolt 68 connected to the locking mechanism and extending longitudinally through the body 14 between the locking mechanism and bracket 20. A cam portion of the overcenter locking mechanism 66 moves the member 28 from its non-sealing position to its sealing position as the handle of the mechanism is pivoted inwardly relative to the adjusting bolt 68. An inner threaded end 70 of the bolt 68 is received in a corresponding threaded bore 72 of the bracket 20 so that the distance between the overcenter mechanism 66 and the bracket can be varied by turning the bolt to adjust the sealing and non-sealing positions of the member 28.

Figure 4:
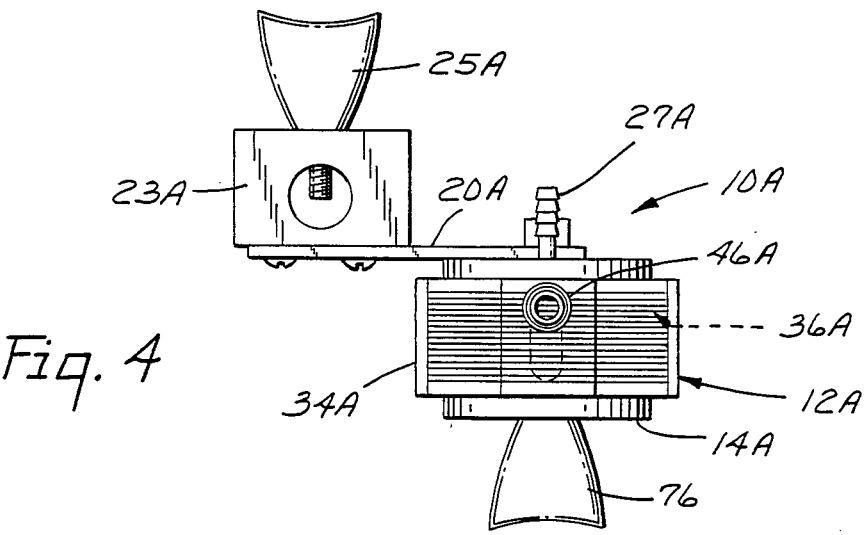
FIG. 4 is top plan view of other embodiments of the combination and heat exchanger of the invention.

FIG. 4 illustrates another embodiment of the invention wherein the heat exchanger, here designated 12A, comprises a generally transparent outer case 34A and undulated, annular barrier 36A sealingly interconnected, but does not include a bubble trap, thermowell or filter. Reference characters ending with an "A" indicate parts of this embodiment that are similar to the parts of the embodiment of FIGS. 1-3 indicated by similar reference numerals not ending with an "A". The heat exchanger 12A is thus designed for use as a heat exchanger within a system that includes some type of bubble trap, filter and temperature sensor separate from the heat exchanger. The internal volume of the blood or cardioplegia solution path portion of the heat exchanger 12A may be smaller than is the case with a heat exchanger that includes a bubble trap, temperature sensor and/or filter, with the result that the heat exchanger 12A requires a smaller volume of blood or solution to be primed than many other heat exchangers.

The combination fluid path and mount of FIG. 4 is designated 10A, and it includes another type of releasable locking means (e.g., a wing-headed bolt 76) for pulling a member (not shown) similar to the frustoconical member 28 into the body 14A of combination 10A. A closed O-shaped clamp 23A and operating screw 25A are provided adjacent the end of the bracket 20A opposite the body 14A for mounting the combination 10A on a support stand (not shown).

Figure 6:
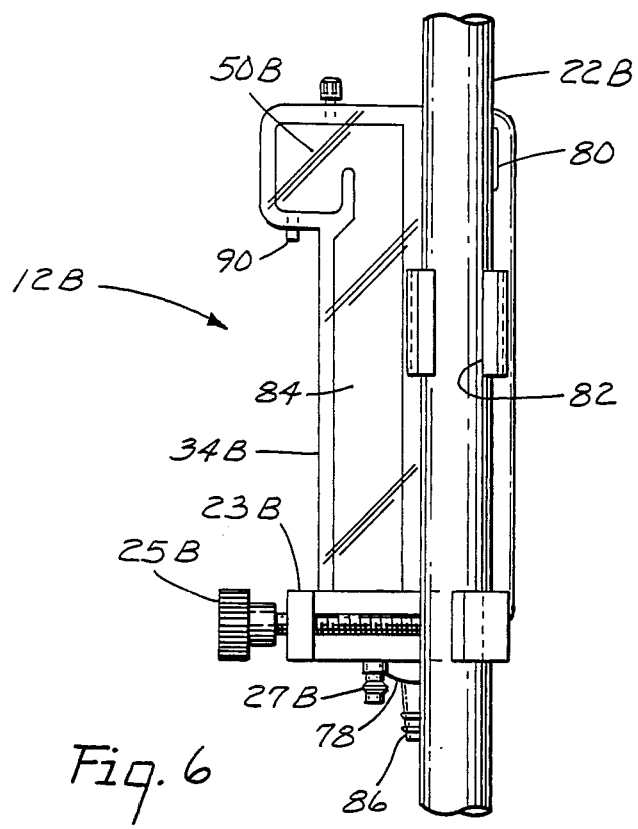
FIG. 6 is a rear elevation of the combination and heat exchanger of FIG. 5.
Figure 7:
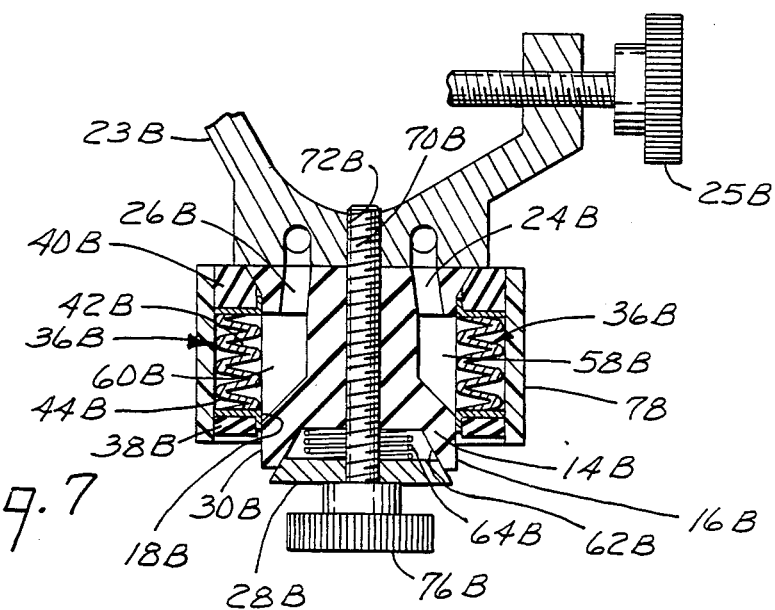
FIG. 7 is a cross-sectional view substantially along line 7—7 of FIG. 5.

FIGS. 5-7 illustrate yet another embodiment of the invention including a number of features similar to those described in coassigned U.S. Pat. No. 4,568,330, which is incorporated herein by reference, in combination with a heat exchanger 12B. A cardioplegia delivery system incorporating many of the features described in the aforesaid U.S. patent is sold under the trade designation "MP-4 Cardioplegia Delivery System" by Sarns, Inc. of Ann Arbor, Mich., a subsidiary of Minnesota Mining and Manufacturing Co., of St. Paul, Minn. Reference characters ending with a "B" indicate parts of this embodiment that are similar to the parts of the embodiments of FIGS. 1-4 indicated by similar reference numerals not ending with a "B". The heat exchanger 12B includes a heat-exchanging portion 78 adjacent the bottom of the heat exchanger having an undulated, annular barrier 36B similar to the barriers 36 and 36A for separating blood or cardioplegia solution from heat-exchanging fluid while permitting heat transfer therebetween. The barrier of portion 78 has an inner, undulated surface 42B defining a generally cylindrical passageway 18B similar to passageway 18 of heat exchanger 12, in which heat-exchanging fluid is circulated and which is adapted for receiving the body 16B of a combination 10B fluid path and mount. By turning a knurled-head bolt 76B, the member 28B is pulled axially inwardly (upwardly in FIG. 7) relative to the body 16B to its sealing position in the recess 62B such that an expandable portion 30B of the body's periphery 16B is expanded radially outwardly against the inner surface 42B of the barrier 36B to seal the passageway 18B of the heat exchanger 12B. Alternatively, an overcenter locking mechanism similar to the overcenter locking mechanism 66 of FIGS. 1 and 2 may be provided.

An outer case 34B of the heat exchanger 12B includes a manometer 80 for measuring the pressure of the blood or cardioplegia solution and a bubble trap 50B adjacent the top of the case for removing gas from the blood or cardioplegia solution. The case 34B is of generally transparent or translucent material to provide a visual indication of the gas removed from the blood or cardioplegia solution and the level of the blood or solution in the manometer 80. A clip 82 may be provided on the back surface 84 (FIG. 6) of the case 34B adjacent the top of the case for securing the top of the heat exchanger 12B to a support stand 22B. In use, blood or cardioplegia solution enters the case 34B through an inlet 86 at the bottom of the heat exchanging portion 78 of the case, flows upwardly along the outer surface 44B of the barrier 36B where its temperature is changed as desired, and passes through a port 89 between the heat exchanging portion and the upper section of the case 34B. The blood or solution then flows upwardly along a temperature sensing strip 88 into the bubble trap 50B, and finally exits through outlet 90 adjacent the downstream end of the bubble trap.

As various changes could be made in the above constructions without departing from the scope of the invention, it is intended that all matter contained in the above description or shown in the accompanying drawings shall be interpreted as illustrative and not in a limiting sense.

What is claimed is:

1. A combination fluid path and mount for a heat exchanger of the type used to cool or heat blood or solution for cardioplegia by transferring heat between the blood or solution and a heat-exchanging fluid, the heat exchanger having an inner surface defining a passageway in which the heat-exchanging fluid flows, the combination comprising a body of generally flexible-resilient material having a periphery adapted to be received in the passageway of the heat exchanger, and means for mounting the body on a support, the body having heat-exchanging fluid inlet and outlet passageways for circulating heat-exchanging fluid to the passageway of the heat exchanger, fixing-sealing means for removably fixing the heat exchanger to the body and sealing between the body and the inner surface of the heat exchanger including means for expanding a portion of the periphery of the body against the inner surface of the heat exchanger to form a seal therebetween and to hold the heat exchanger on the body.

2. A combination according to claim 1 wherein the body is generally cylindrical, the means for expanding a portion of the body includes a tapered means for expanding the portion of the body radially outwardly, the body having a recess at one end thereof for receiving the tapered means such that a portion of the body adjacent the recess is expanded radially outwardly by the tapered means.

3. A combination according to claim 2 wherein the means for mounting the body on a support includes a bracket attached to the end of the body opposite the recess and clamp means on the bracket for clamping a support stand to mount the body thereon, the fixing-sealing means includes a releasable locking means for pulling the tapered means toward the bracket into the recess of the body and holding it in the recess, the releasable locking means including an overcenter locking mechanism for securely holding the tapered means in the recess, and an adjusting bolt connected to the locking mechanism and the bracket and extending longitudinally through the body between the locking mechanism and bracket, the heat-exchanging fluid inlet and outlet passageways having openings formed in the circumferential surface of the body along opposite sides of the body for supplying the heat-exchanging fluid to the heat exchanger and removing the fluid from the heat exchanger, the openings being elongate in the direction longitudinally or axially of the body.

4. A combination according to claim 2 wherein the means for expanding a portion of the body includes spring means for biasing the tapered means longitudinally or axially outwardly from the recess of the body to a non-sealing position wherein the heat exchanger can be placed on the body with the body received in the heat exchanger and the heat exchanger can be removed from the body, the tapered means being movable against the spring bias longitudinally or axially inwardly into the recess to a sealing position wherein the portion of the body adjacent the recess is expanded radially outwardly by the tapered means to hold and seal the heat exchanger.

5. A combination according to claim 4 wherein the tapered means includes a frustoconical member adapted to be received in the recess of the body such that the portion of the body adjacent the recess is expanded radially outwardly by the frustoconical member.

6. A combination according to claim 5 wherein the fixing-sealing means includes releasable locking means for pulling the frustoconical member into the recess of the body and holding it in sealing position, the releasable locking means including an overcenter locking mechanism for securely holding the frustoconical member in sealing position.

7. A combination according to claim 4 wherein the body is formed of generally elastomeric material having a Shore A durometer of between 60 and 90.

8. A combination according to claim 4 wherein the means for mounting the body on a support includes a bracket attached to the end of the body opposite the recess and clamp means on the bracket for clamping a support stand to mount the body thereon.

9. A combination according to claim 8 wherein the generally cylindrical body is flared radially outwardly adjacent the bracket.

10. A combination according to claim 8 wherein the heat-exchanging fluid inlet and outlet passageways have openings formed in the circumferential surface of the body along opposite sides of the body for supplying the heat-exchanging fluid to the heat exchanger and removing the fluid from the heat exchanger, the openings being elongate in the direction longitudinally or axially of the body.

11. A combination according to claim 1 further including a heat exchanger for cooling or heating blood or cardioplegia solution by transferring heat between the blood or solution and the heat-exchanging fluid, the heat exchanger including an inner surface defining a passageway in which heat-exchanging fluid may be circulated, the passageway of the heat exchanger being adapted to receive the body for mounting the heat exchanger thereon and providing the heat-exchanging fluid to the heat exchanger.

12. A combination according to claim 11 wherein the body is generally cylindrical, the heat exchanger including an undulated, annular barrier for separating the blood or cardioplegia solution from the heat-exchanging fluid while permitting heat transfer through the barrier, the barrier having an inner undulated surface constituting the inner surface and defining the body receiving passageway as generally cylindrical, and an outer undulated surface along which the blood or solution flows.

13. A combination according to claim 12 wherein the heat exchanger further includes a case sealingly connected to the barrier and forming a blood or cardioplegia solution path along the barrier through the case, the case including a bubble trap at one end of the blood or solution path for separating and trapping gas from the blood or solution, the heat exchanger being adapted to be turned on the cylindrical body between a priming position wherein the bubble trap is positioned below the body and a ready position wherein the bubble trap is positioned above the body.

14. A combination according to claim 12 wherein the heat exchanger further includes a case sealingly connected to the barrier and forming a blood or cardioplegia solution path along the barrier through the case, the case including a manometer for measuring the pressure of the blood or solution and a bubble trap for removing bubbles from the blood or solution, the case being of generally transparent or translucent material to provide a visual indication of the gas removed from the blood or solution.

15. A heat exchanger for heating or cooling blood or solution for cardioplegia by transferring heat between the blood or solution and a heat-exchanging fluid, the heat exchanger being adapted to be mounted on a combination fluid path and mount including a body of generally flexible-resilient material having a periphery, the body having heat-exchanging fluid inlet and outlet passageways each opening through the periphery for circulating heat-exchanging fluid to the heat exchanger, and fixing-sealing means for removably fixing the heat exchanger to the body and sealing between the body and heat exchanger including means for expanding a portion of the periphery of the body against the heat exchanger to form a seal therebetween and to hold the heat exchanger on the body; the heat exchanger comprising an outer case having an inlet and outlet for blood or cardioplegia solution, and a barrier sealingly connected to the case for separating the blood or cardioplegia solution from the heat-exchanging fluid while permitting heat transfer through the barrier, the barrier having an inner surface forming a passageway in which heat-exchanging fluid may be circulated, the passageway of the heat exchanger being adapted to receive the body of the combination fluid path and mount for mounting the heat exchanger thereon and providing heat-exchanging fluid to the heat exchanger, the inner surface of the barrier being adapted for sealing engagement with the expandable portion of the body.

16. A heat exchanger according to claim 15 wherein the barrier is annular having an inner undulated surface constituting the inner surface and defining the body receiving passageway as generally cylindrical, and an outer undulated surface along which the blood or cardioplegia solution flows.

17. A heat exchanger according to claim 16 wherein the case includes a bubble trap at one end of the blood or solution path for separating and trapping gas from the blood or solution, the heat exchanger being adapted to be turned on the cylindrical body between a priming position wherein the bubble trap is positioned below the body and a ready position wherein the bubble trap is positioned above the body.

18. A heat exchanger according to claim 16 wherein the case includes a manometer for measuring the pressure of the blood or solution and a bubble trap for removing bubbles from the blood or solution, the case being of generally transparent or translucent material to provide a visual indication of the gas removed from the blood or solution.

* * * * *